United States Patent
Sodhi

(10) Patent No.: US 10,064,990 B2
(45) Date of Patent: Sep. 4, 2018

(54) PACKAGELESS SYRINGE ASSEMBLY WITH STERILIZABLE FLUID PATH

(75) Inventor: Anil Sodhi, Clinton, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1256 days.

(21) Appl. No.: 13/549,652

(22) Filed: Jul. 16, 2012
(Under 37 CFR 1.47)

(65) Prior Publication Data

US 2014/0018742 A1 Jan. 16, 2014

(51) Int. Cl.
*A61M 5/00* (2006.01)
*A61L 2/20* (2006.01)

(52) U.S. Cl.
CPC .............. *A61M 5/002* (2013.01); *A61L 2/206* (2013.01); *A61L 2202/23* (2013.01)

(58) Field of Classification Search
CPC ...... A61M 5/001; A61M 5/002; A61M 5/178; A61M 2005/3117; A61M 2005/3118; A61M 2005/312; A61M 2005/3121; A61M 5/5086; A61M 2209/06; A61M 2005/3104; A61M 39/20; A61M 2039/205; A61M 39/16; A61M 39/165; A61M 39/18
See application file for complete search history.

(56) References Cited

U.S. PATENT DOCUMENTS

| RE25,113 E | * | 1/1962 | Wilburn ................. A61M 5/28 604/190 |
| 3,306,291 A | | 2/1967 | Burke |
| 3,434,587 A | | 3/1969 | Ciampa |
| 3,485,239 A | * | 12/1969 | Vanderbeck .......... A61M 5/178 206/365 |
| 3,677,245 A | | 7/1972 | Welch |
| 3,828,775 A | | 8/1974 | Armel |
| 3,930,499 A | * | 1/1976 | Rimbaud ................ A61M 5/24 206/365 |
| 4,121,588 A | | 10/1978 | Geiger |
| 4,148,316 A | | 4/1979 | Xanthopoulos |
| 4,300,678 A | | 11/1981 | Gyure et al. |
| 4,592,744 A | * | 6/1986 | Jagger .................. A61B 5/1405 600/576 |
| 4,929,232 A | * | 5/1990 | Sweeney ............. A61M 5/3202 604/111 |
| 5,147,328 A | * | 9/1992 | Dragosits ............ A61M 5/3129 222/386 |

(Continued)

FOREIGN PATENT DOCUMENTS

| EP | 1166810 | 1/2002 |
| JP | S53-142088 A | 12/1978 |

(Continued)

OTHER PUBLICATIONS

"PCT International Search Report for PCT/US2013/050011", dated Feb. 12, 2013, 5 pages.

(Continued)

*Primary Examiner* — Aarti B Berdichevsky
*Assistant Examiner* — Laura Schell
(74) *Attorney, Agent, or Firm* — Servilla Whitney LLC

(57) ABSTRACT

Syringe assemblies comprising a first cap and a second cap to ensure sterilization of the fluid path without the need for external packaging are described. Also described are methods of sterilizing the fluid path of a syringe assembly.

19 Claims, 6 Drawing Sheets

(56) References Cited

U.S. PATENT DOCUMENTS

| | | | | |
|---|---|---|---|---|
| 5,395,339 | A * | 3/1995 | Talonn | A61M 5/31511 604/110 |
| 6,551,286 | B1 | 4/2003 | Claesens | |
| 6,599,268 | B1 * | 7/2003 | Townsend | A61M 5/3234 604/110 |
| 6,616,636 | B2 | 9/2003 | Lee | |
| 8,043,267 | B2 | 10/2011 | Nanba et al. | |
| 2002/0052577 | A1 * | 5/2002 | Shimazaki | A61M 5/3129 604/192 |
| 2002/0068909 | A1 | 6/2002 | Alchas et al. | |
| 2005/0226763 | A1 * | 10/2005 | Raynal-Olive | A61L 2/208 422/28 |
| 2008/0167624 | A1 * | 7/2008 | Weston | A61M 5/002 604/198 |
| 2009/0095290 | A1 * | 4/2009 | Cain | A61L 2/206 128/202.22 |
| 2009/0131864 | A1 * | 5/2009 | Pickhard | A61M 5/284 604/83 |
| 2009/0281504 | A1 * | 11/2009 | Nanba | A61M 5/28 604/190 |
| 2009/0287158 | A1 | 11/2009 | Hund et al. | |
| 2010/0012537 | A1 * | 1/2010 | Farrar | A61M 5/002 206/364 |
| 2011/0190709 | A1 * | 8/2011 | Mitsuno | A61M 5/001 604/181 |
| 2012/0041381 | A1 * | 2/2012 | Raj | A61M 5/002 604/192 |
| 2012/0117920 | A1 | 5/2012 | Mermet et al. | |

FOREIGN PATENT DOCUMENTS

| | | |
|---|---|---|
| JP | Hei 2-283376 A | 11/1990 |
| JP | Hei 3-18375 A | 1/1991 |
| JP | 2002085562 A | 3/2002 |
| JP | 2006314554 A | 11/2006 |

OTHER PUBLICATIONS

Extended European Search Report in EP 17168216.4 dated Aug. 16, 2017, 6 pages.

* cited by examiner

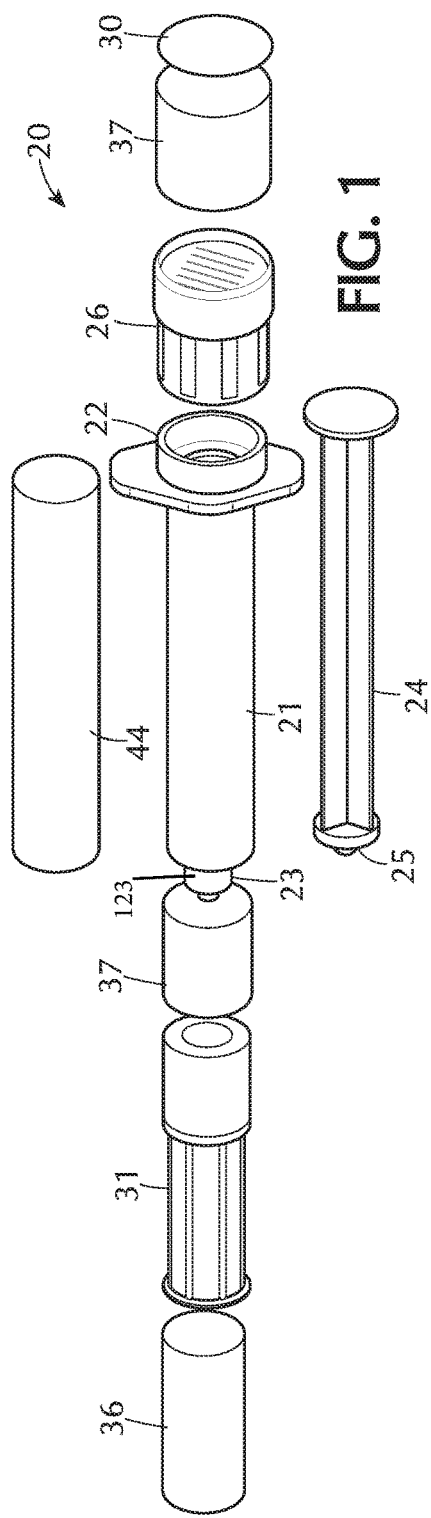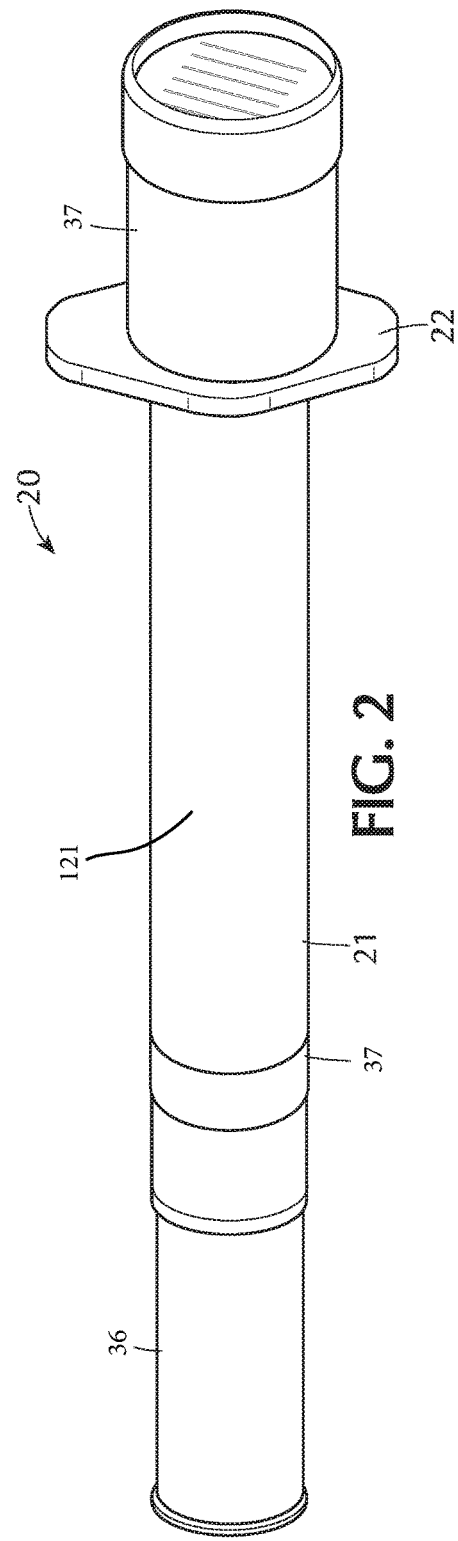

ated and is in flow communication with the fluid path and permitting sterilization of a portion of the fluid path by radiation or a gas, and an open distal end affixed to the proximal end of the barrel, wherein the first cap proximal end is optionally covered by a first permeable material. In one or more embodiments, the first permeable material comprises Tyvek® or a medical grade material with a porosity of 8-400 seconds/100 mL. In one or more embodiments, the proximal end of the first cap includes a circumferential lip defining a recess containing a first permeable material. In a specific embodiment, the first cap includes an interior surface having a plurality of tortuous path rings.

PACKAGELESS SYRINGE ASSEMBLY WITH STERILIZABLE FLUID PATH

TECHNICAL FIELD

The present invention relates to syringe assemblies, and more particularly to syringe assemblies in which the fluid path can be maintained in sterile condition without the presence of external packaging surrounding the syringe assembly.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the sterile article, such as with a blister pack housing a syringe assembly, so as to minimize the time period in which the sterile article is exposed to unsterile conditions.

When the packaging used to protect sterile articles such as syringe assemblies is opened and the syringe assembly is removed, the packaging then needs to be discarded, leading to an increase in the amount of waste material produced in a hospital or other medical setting. Additionally, when packaging is used to contain each individual syringe assembly or a number of syringe assemblies, the cost of providing the packaging contributes significantly to the cost of each syringe assembly product. It is desired that a syringe assembly be manufactured at as low a cost as possible, thus reducing the price at which the syringe assembly can be sold.

In addition to the costs associated with external packaging, packaging used to protect sterile articles tends to be bulky and, consequently, consumes more storage space per unit than is desirable. Thus, the use of packaging to contain the syringe assembly adds additional and unnecessary bulk to each individual syringe assembly. This additional bulk significantly detracts from valuable storage space in a hospital or other medical storage area.

It would be advantageous to provide a syringe assembly consisting of the usual components that does not provide packaging surrounding the syringe assembly, but is able to maintain a sterile fluid path prior to use.

SUMMARY

Embodiments of the present invention are directed to a packageless syringe assembly. Syringe assemblies according to a first aspect of the present invention include a plunger rod, a syringe barrel, and a first and second cap that permit sterilization of a portion of the fluid path by radiation or a gas. The features providing for sterilization of the fluid path allow the fluid path to remain sterile without the need for external packaging material surrounding the syringe assembly.

In one or more embodiments, the barrel includes a side wall having an outside surface and an inside surface defining a chamber for retaining fluid, an open proximal end, and a distal end including a distal wall, the chamber, distal end and proximal end defining a fluid path.

In one or more embodiments, the plunger rod includes a stopped disposed within the barrel.

In one or more embodiments, the first cap has a proximal end having a first segment that is radiation and gas perme- In one or more embodiments, the second cap is affixed to the distal end of the barrel, and the second cap has a proximal end and a closed distal end having a segment that is radiation and gas permeable and is in flow communication with the fluid path and permitting sterilization of a portion of the fluid path by radiation or a gas. In one or more embodiments, the second cap includes an interior surface having a plurality of tortuous path rings.

In one or more embodiments, a collar is attached to the closed distal end of the second cap, the collar comprising a second permeable material that covers the closed distal end of the second cap.

In one or more embodiments, a tamper-evident band covers a portion of at least one of the first and second cap.

In one variant, the first or second cap can comprise a plurality of openings in flow communication with the fluid path and permit sterilization of a portion of the fluid path using radiation or a gas. In one or more embodiments, the plurality of openings are selected from holes or slots.

In one or more embodiments, the first cap comprises a plurality of openings on the first segment that are radiation and gas permeable and are in flow communication with the fluid path by radiation or a gas. In one or more embodiments, the plurality of openings are selected from holes or slots.

In one or more embodiments, the second cap comprises a plurality of openings on the second segment of the second cap that are radiation and gas permeable ad in flow communication with the fluid path and permitting sterilization of a portion of the fluid path by radiation or a gas. In one or more embodiments, the plurality of openings are selected from holes or slots.

In one or more embodiments, the syringe assembly is not surrounded by any external packaging. The external packaging can be a blister pack.

In one or more embodiments, the syringe assembly is sterile.

In one or more embodiments, the first cap is attached to the barrel using at least one heat stake. In one or more embodiments, the second cap is attached to the barrel using at least one heat stake.

In one or more embodiments, the surface of the barrel has a matte finish. In one or more embodiments, the first cap has a matte finish. In one or more embodiments, the second cap has a matte finish. In one or more embodiments, the barrel further comprises a transparent label affixed to the outer surface of the side wall of the barrel.

In one or more embodiments, the syringe assembly is stored inside a Tyvek® bag with a plurality of other packageless syringe assemblies.

In one or more embodiments, each of the first and second caps is covered with a tamper-evident band.

A second aspect of the present invention is directed to a packageless syringe assembly including a fluid path that can be sterilized by gas or radiation comprising a barrel a barrel including a side wall having an outside surface and an inside surface defining a chamber for retaining fluid, an open proximal end, and a distal end including a distal wall, the chamber, distal end and proximal end defining a fluid path; a plunger rod including a stopper disposed within the barrel; a first cap having a proximal end having a plurality of openings in flow communication with the fluid path and permitting sterilization of a portion of the fluid path by radiation or a gas and an open distal end affixed to the proximal end of the barrel, wherein the first cap proximal end is covered by a first permeable material; a second cap affixed to the distal end of the barrel, the second cap having a proximal end and a closed distal end with a plurality of openings in flow communication with the fluid path and permitting sterilization of a portion of the fluid path by radiation or a gas; a collar attached to the closed distal end of the second cap, the collar comprising a second permeable material that covers the openings on the closed distal end of the second cap; and a tamper-evident band covering a portion of at least one of the first and second cap.

A further aspect of the present invention pertains to a method of sterilizing the fluid path of a syringe assembly. The method according to one embodiment comprises using radiation or a gas to sterilize the fluid path of a syringe assembly, wherein the syringe assembly includes a plunger rod, a syringe barrel, and a first and second cap that permit sterilization of a portion of the fluid path by radiation or a gas. The method allows the fluid path to remain sterile without the need for external packaging material surrounding the syringe assembly.

In one or more embodiments, the barrel includes a side wall having an outside surface and an inside surface defining a chamber for retaining fluid, an open proximal end, and a distal end including a distal wall, the chamber, distal end and proximal end defining a fluid path.

In one or more embodiments, the plunger rod includes a stopped disposed within the barrel.

In one or more embodiments, the first cap has a proximal end having a first segment that is radiation and gas permeable and is in flow communication with the fluid path and permitting sterilization of a portion of the fluid path by radiation or a gas, and an open distal end affixed to the proximal end of the barrel, wherein the first cap proximal end is optionally covered by a first permeable material.

In one or more embodiments, the second cap is affixed to the distal end of the barrel, and has a proximal end and a closed distal end having a second segment that is radiation and gas permeable and is in flow communication with the fluid path and permitting sterilization of a portion of the fluid path by radiation or a gas.

In one or more embodiments, a collar is attached to the closed distal end of the second cap, the collar comprising a second permeable material that covers the closed distal end of the second cap; and a tamper-evident band covering a portion of at least one of the first and second cap.

In one or more embodiments, the radiation is selected from E-beam and cobalt.

In one or more embodiments, the gas is ethylene oxide.

BRIEF DESCRIPTION OF THE DRAWINGS

FIG. 1 is a perspective view of an assembled syringe assembly according to an embodiment of the present invention;

FIG. 2 is an exploded perspective view of a syringe assembly according to an embodiment of the present invention;

DETAILED DESCRIPTION

Figure 3A:
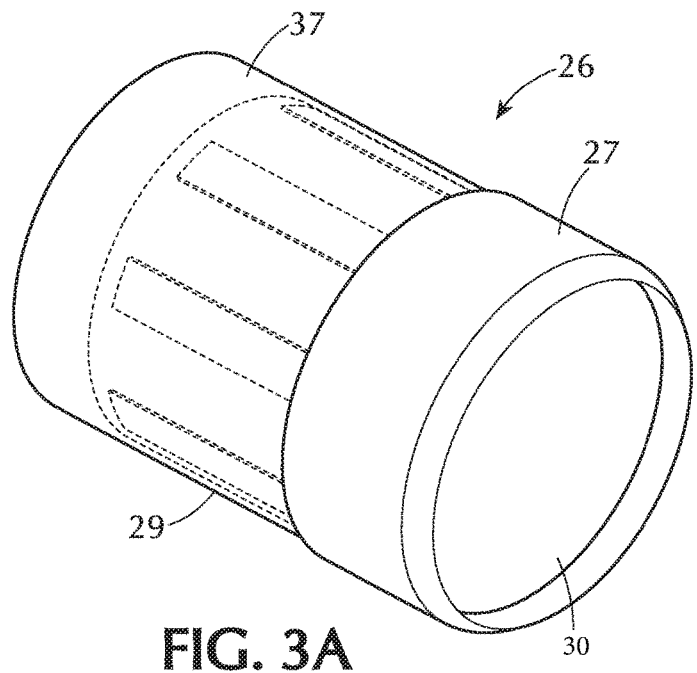
FIG. 3A is an end view of the first cap which attaches to the syringe assembly of FIG. 1.

Before describing several exemplary embodiments of the invention, it is to be understood that the invention is not limited to the details of construction or process steps set forth in the following description. The invention is capable of other embodiments and of being practiced or being carried out in various ways.

With respect to terms used in this disclosure, the following definitions are provided.

Reference to "syringe assembly" includes syringes that are indicated for use with needles, nozzle, tubing, or for use in flush systems.

As used herein, the use of "a," "an," and "the" includes the singular and plural.

As used herein, the term "packageless" refers to syringe assemblies that are not surrounded by external packing material, including, but not limited to, flexible and rigid blister packs.

As used herein, the term "tortuous path" refers to a long known principle established by Louis Pasteur. In experiments, Pasteur fashioned glass flasks with various neck shapes. Each flask contained an enclosed sterile media. The necks on some flasks allowed microorganisms to fall on the contained media, which then became contaminated as evidenced by bacterial growth. The media in flasks with S-curved necks, or in those flasks which presented a "tortuous path" for microorganisms, remained sterile. The microorganisms were stopped at the openings to the curved necks, as well as at the curves in the necks.

As used herein, the term "tortuous path ring" refers to a ring, circle, loop, band, sphere, etc. that creates a barrier between the contaminated exterior and the sterile interior region of the syringe assembly by creating a extended pathway with a plurality of interruptions that prevents the migration of microorganisms from the outside of the syringe assembly into the sterile fluid path.

As used herein, the term "microorganism" refers to a microbe or organism that is unicellular or lives in a colony of cellular organisms. Microorganisms are very diverse; they include, but are not limited to bacteria, fungi, archaea, and protozoans.

As used herein, the terms "heat staking" and "heat stake" refer to a process of connecting two components by creating an interference fit between the two pieces. A plastic stud protruding from one component fits into the hole in a second component. The plastic stud is then deformed through the softening of the plastic via heat to form a head which mechanically locks the two components together.

As used herein, the term "permeable material" refers to any medical grade material such as a paper or fabric which is breathable and permeable to gas, but is not permeable to microorganisms. Medical grade packaging materials such as papers or woven materials have a typical porosity between 8 and 400 seconds/100 mL as defined by ASTM D-726 or ISO 5636. These materials must provide a microbial barrier as defined by ASTM F-1608 and/or F-2638. These materials can be provided with an antimicrobial agent or disinfectant integral with or converted coating of the material. Medical grade materials can include, but are not limited to, medical grade papers and Tyvek®. Typical suppliers can include, but are not limited to, Arjo-Wiggins, Billerud, Domtar, Neenah, Hansol, and Dupont.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

As used herein, the terms "antimicrobial agent" or "antimicrobial" refers to substances that kill or inhibit the growth of microorganisms such as bacteria, fungi, archaea, or protozoans. Antimicrobial agents either kill microbes, or prevent the growth of microbes.

As used herein, the term "disinfectant" refers to antimicrobial substances that are used on non-living objects or outside the body, e.g., on the skin.

Disinfectants or antimicrobial agents can include, but are not limited to, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorohexidine, dichlorobenzyl alcohol, dehydroacetic acid, hexetidine, triclosan, hydrogen peroxide, colloidal silver, and mixtures thereof.

As used herein, the term "sterilization" refers to a means of eliminating or killing microorganisms present on a surface, contained in a fluid, or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, orthophthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

As used herein, the terms "ethylene oxide" or "EO" or "EtO" refer to a gas that is commonly used to sterilize objects sensitive to temperatures greater than 65° C. and/or radiation, such as plastics, optics and electrics. Ethylene oxide sterilization is generally carried out between 30° C. and 65° C. with relative humidity above 30% and a gas concentration between 200 and 1000 mg/L. Typical EtO exposure lasts for at least two or more hours with additional time allowed for pre and post conditioning. Ethylene oxide is highly effective at sterilization and penetrates well, moving through permeable papers, cloth, and some plastic films. Ethylene oxide can kill all known microorganisms, including viruses, bacteria, and fungi. Ethylene oxide is highly flammable, toxic, and carcinogenic.

Ethylene oxide sterilization typically consists of a preconditioning phase, the actual sterilization run, and a period of post-sterilization aeration to remove toxic residues, such as ethylene oxide residues and by-products such as ethylene glycol and ethylene chlorohydrine. The two most significant ethylene oxide sterilization methods as: (1) the gas chamber method, and (2) the micro-dose method. The gas chamber method involves flooding a large chamber with a combination of ethylene oxide and other gases used as dilutants. This method has drawbacks inherent to the use of large amounts of ethylene oxide being releases into a large space, including air contamination produced by CFCs and/or large amounts of ethylene oxide residuals, flammability and storage issues calling for special handling and storage, operator exposure risk and training costs.

Gamma rays are very penetrating and are commonly used for sterilization of disposable medical equipment, such as syringes, needles, cannulas, and IVs. Gamma radiation requires bulky shielding for the safety of the operators; it also requires storage of a radioisotope (usually Cobalt-60), which continuously emits gamma rays.

As used herein, the term "cobalt" or "cobalt-60" refers to cobalt-60, which is a synthetic radioactive isotope of cobalt; it is a hard, gray-blue metal and might appear as small metal disks or in a tube, enclosed at both ends, that holds the small disks. Cobalt-60 can occur as a powder if the solid sources have been ground or damaged. Cobalt-60 is used medically for radiation therapy as implants and as an external source of radiation exposure. Cobalt-60 is also used industrially in leveling gauges and to x-ray welding seams and other structural elements to detect flaws. Additionally, cobalt-60 is used for food irradiation and other sterilization processes. Cobalt-60 decays by gamma radiation. External exposure to large sources of Cobalt-60 can cause skin burns, acute radiation sickness, or death As used herein, the term "E-beam" refers to electron beam (E-beam) processing, which is commonly used for medical sterilization. Electron beams use an on-off technology and provide a much higher dosing rate than gamma or x-rays. Due to the higher dose rate, less exposure time is needed, and, thereby, any potential degradation to polymer materials is reduced. A limitation is that electron beams are less penetrating than either gamma rays or x-rays.

Provided are syringe assemblies that include a plunger rod and a syringe barrel and a first and second cap, that incorporate elements for sterilizing the fluid path without the need for external packaging surrounding the syringe assembly. The assembled syringe is shown in FIG. 1, with the components and alternative embodiments of the present invention shown in FIGS. 2-8. Referring to FIGS. 1 and 2, a packageless syringe assembly 20 according to the present invention includes a fluid path that can be sterilized by gas or radiation and generally comprises a barrel 21, including a side wall having an outside surface and an inside surface for defining a chamber 121 for retaining fluid. The barrel 21 further includes an open proximal end 22 and a distal end 23 including a distal wall 123, the chamber, distal end 23 and proximal end 22 defining a fluid path.

A plunger rod 24 including a stopper 25 that is slidably positioned in fluid-tight engagement with the inside surface of the barrel for drawing fluid into and driving fluid out of the chamber by movement of the stopper 25 relative to the barrel 21, the plunger rod 24 extending outwardly from the open proximal end 22 of the barrel.

Referring to FIG. 3A, in one or more embodiments, a first cap 26 including a proximal end 27 having a first segment 28 that is radiation and gas permeable and is in flow communication with the fluid path permitting sterilization of a portion of the fluid path by radiation or a gas, an open distal end 29 affixed to the proximal end 22 of the barrel 21.

Figure 3B:
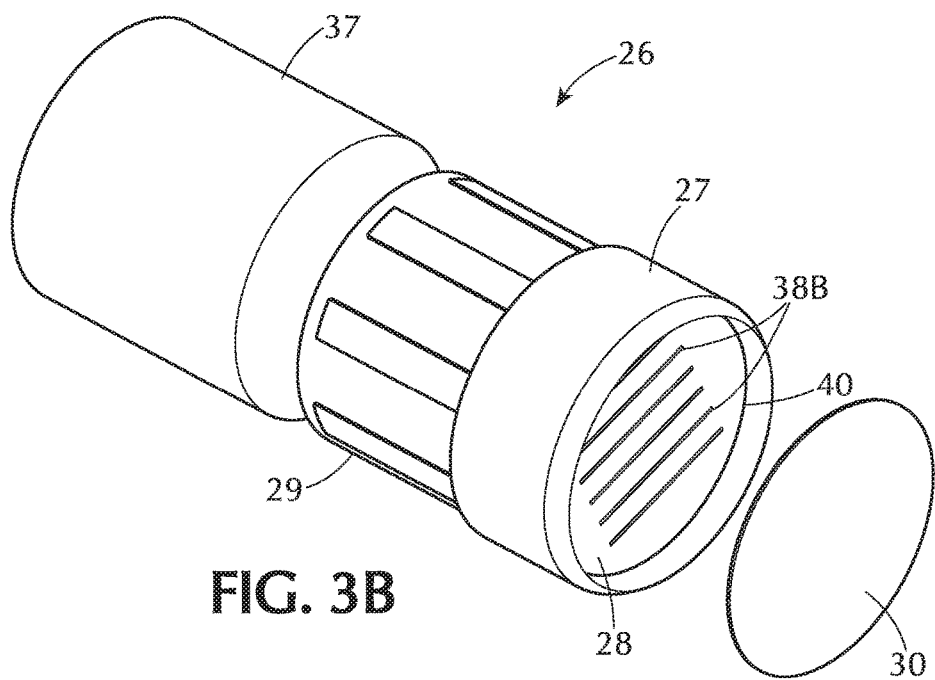
FIG. 3B is an end view of the first cap which attaches to the syringe assembly of FIG. 1.

Referring to FIG. 3B, in one or more embodiments, the first cap proximal end 27 is optionally covered by a first permeable material 30. In one or more embodiments, the first permeable material 30 comprises a medical grade paper with a porosity of 30-400 seconds/100 mL or Tyvek® with a porosity of 8-40 seconds/100 mL. Both materials are porous for breathability, but also provide a microbial barrier. A tamper evident band 37 may cover a portion of the open distal end 29 of the first cap 26. The proximal end 27 of the first cap 26 may include a circumferential lip 40 defining a recess containing the first permeable material 30. The packageless syringe assembly 20 can further comprise a plurality of openings 38B on the first segment 28 of the first cap 26 that are radiation and gas permeable and are in flow communication with the fluid path and permitting sterilization of a portion of the fluid path by radiation or a gas. In a specific embodiment, the plurality of openings 38B comprise slots.

Figure 3C:
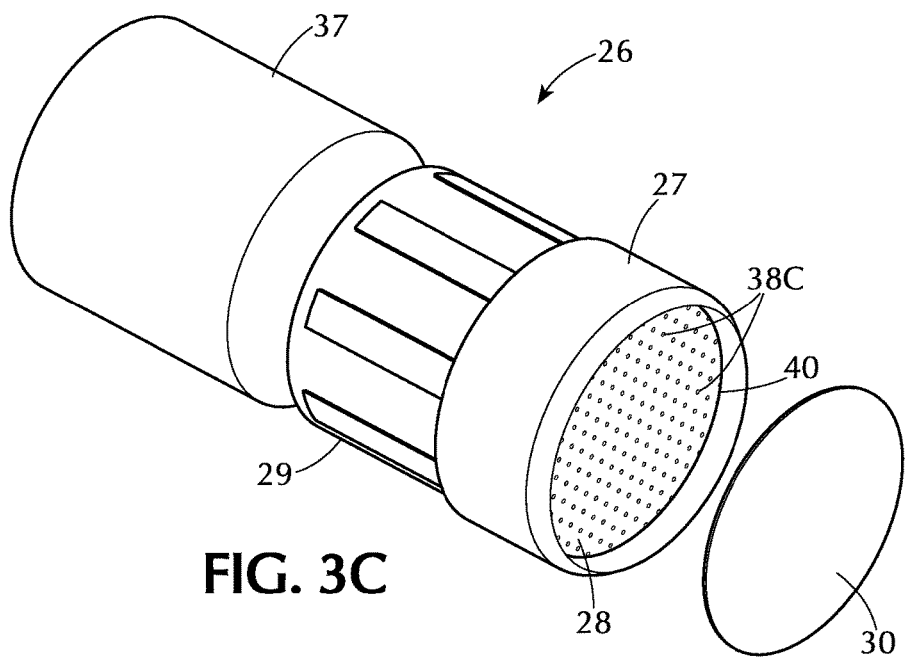
FIG. 3C is an end view of the first cap which attaches to the syringe assembly of FIG. 1.

Referring to FIG. 3C, in one or more embodiments, the first cap proximal end 27 is optionally covered by a first permeable material 30. In one or more embodiments, the first permeable material 30 comprises a medical grade paper with a porosity of 30-400 seconds/100 mL or Tyvek® with a porosity of 8-40 seconds/100 mL. Both materials are porous for breathability, but also provide a microbial barrier. A tamper evident band 37 may cover a portion of the first cap. The proximal end 27 of the first cap 26 may include a circumferential lip 40 defining a recess containing the first permeable material 30. The packagless syringe assembly 20 can further comprise a plurality of openings 38C on the first segment 28 of the first cap 26 that are radiation and gas permeable and are in flow communication with the fluid path and permitting sterilization of a portion of the fluid path by radiation or a gas. In a specific embodiment, the plurality of openings 38C comprise holes.

Figure 4:
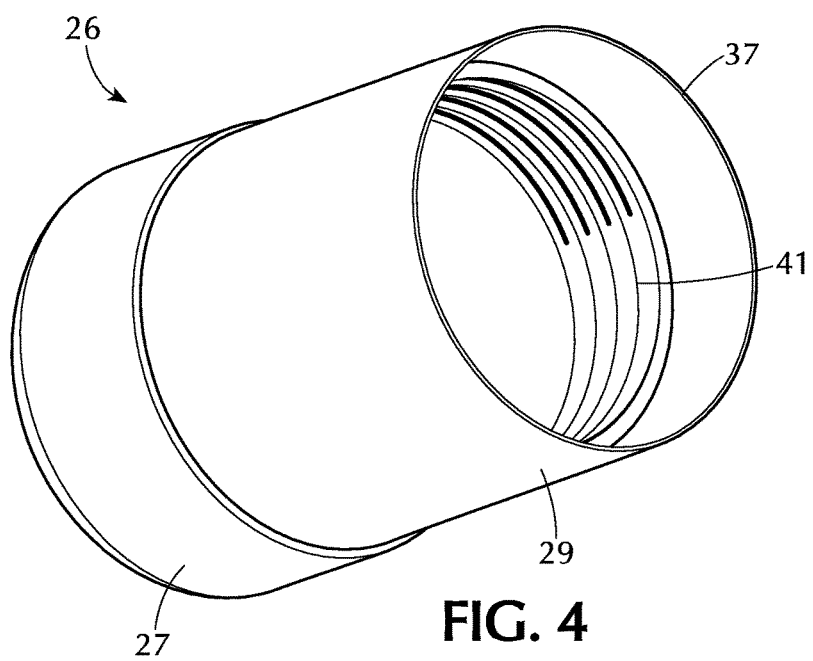
FIG. 4 is an end view of the first cap which attaches to the syringe assembly of FIG. 1.
Figure 5:
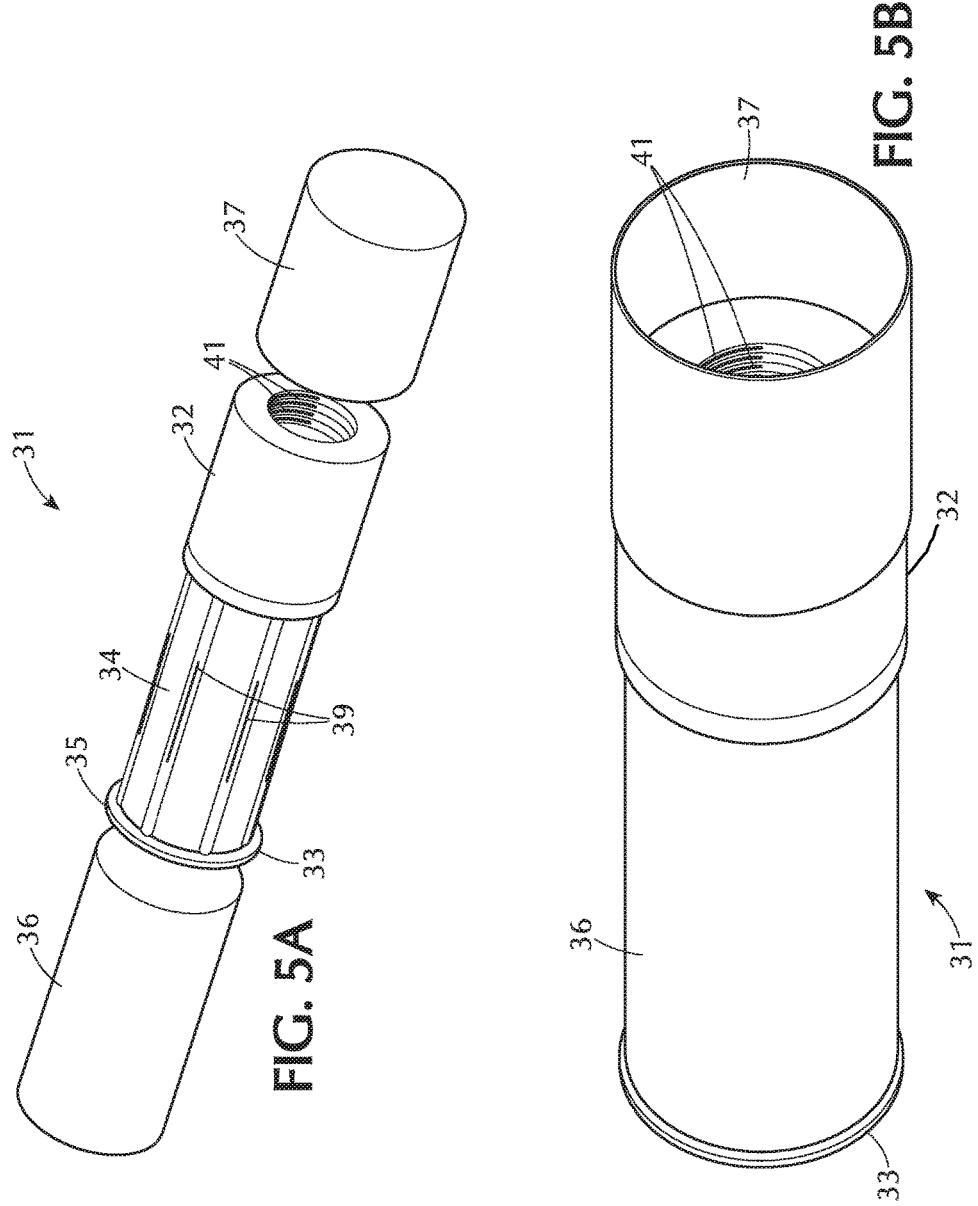
FIG. 5A is an end view of the second cap attaches to the syringe assembly of FIG. 1.
FIG. 5B is an end view of the second cap which attaches to the syringe assembly of FIG. 1.

Referring to FIG. 4 the first cap 26 may include an interior surface having a plurality of tortuous path rings 41. The tortuous path rings 41 create a barrier between the contaminated exterior and the sterile interior region of the syringe assembly by creating a long pathway with a plurality of interruptions that prevents the migration of microorganisms from the outside of the syringe assembly into the sterile fluid path. The first cap 26 may also include a tamper evident band 37 covering a portion of the open distal end 29 of the first cap.

Referring to FIGS. 5A and 5B, a second cap 31 affixed to the distal end 23 of the barrel 21, the second cap 31 having a proximal end 32 and a distal end 33 having a second segment 34 that is radiation and gas permeable and is in flow communication with the fluid path and permitting sterilization of a portion of the fluid path or a gas. The second cap 31 may include an interior surface having a plurality of tortuous path rings 41. The tortuous path rings 41 create a barrier between the contaminated exterior and the sterile interior region of the syringe assembly by creating a long pathway with a plurality of interruptions that prevents the migration of microorganisms from the outside of the syringe assembly into the sterile fluid path.

Optionally, a collar 35 is attached to the distal end 33 of the second cap 31, the collar 35 comprising a second permeable material 36 that covers the closed distal end 33 of the second cap 31; and a tamper evident band 37 covering a portion of at least one of the first cap 26 and the second cap 31.

The packageless syringe assembly 20 can further comprise a plurality of openings 39 on the second segment 34 of the second cap 31 that are radiation and gas permeable and are in flow communication with the fluid path and permitting sterilization of a portion of the fluid path by radiation or a gas. In a specific embodiment, the plurality of openings are selected from holes and slots.

Figure 6:
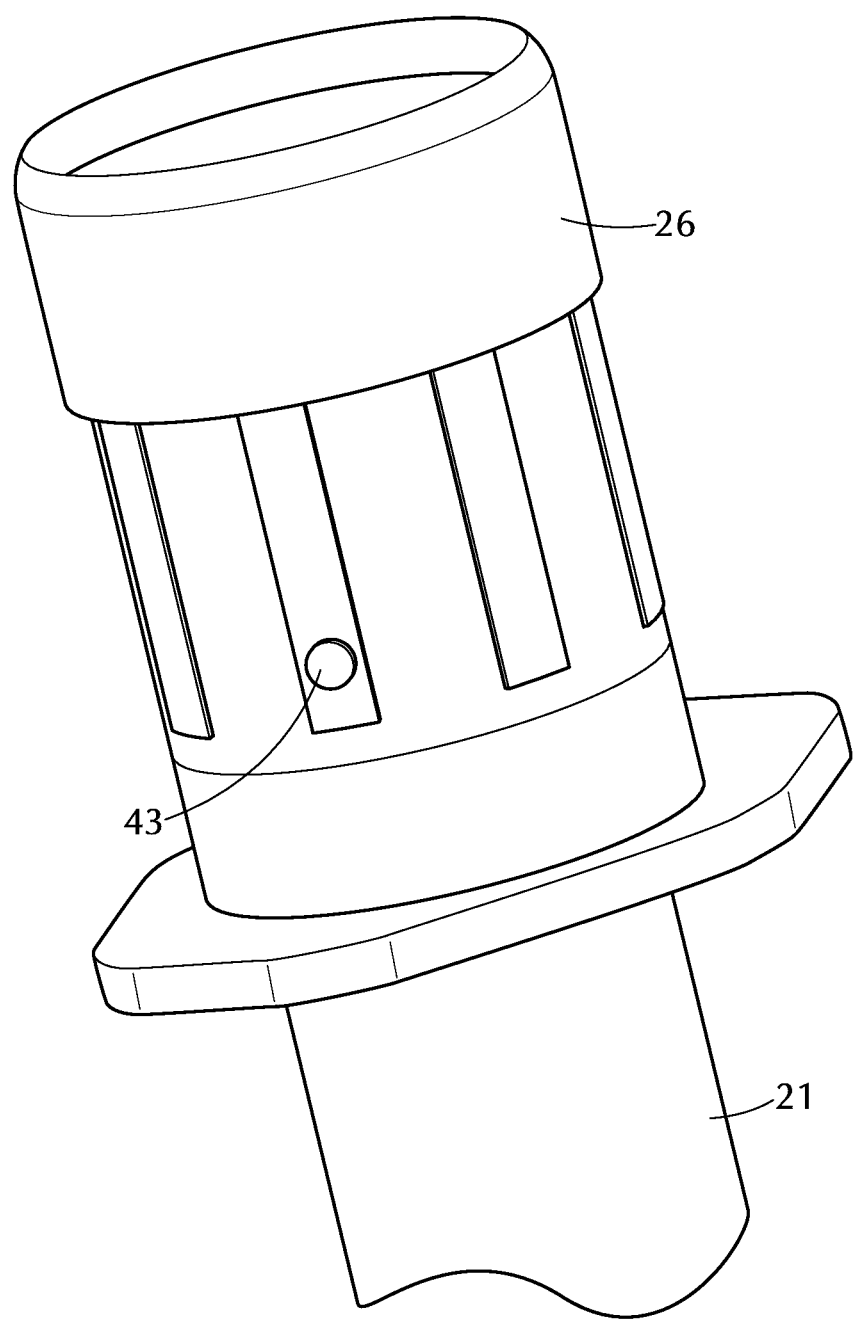
FIG. 6 is a perspective view of the first cap which attaches to the syringe assembly of FIG. 1.
Figure 7:
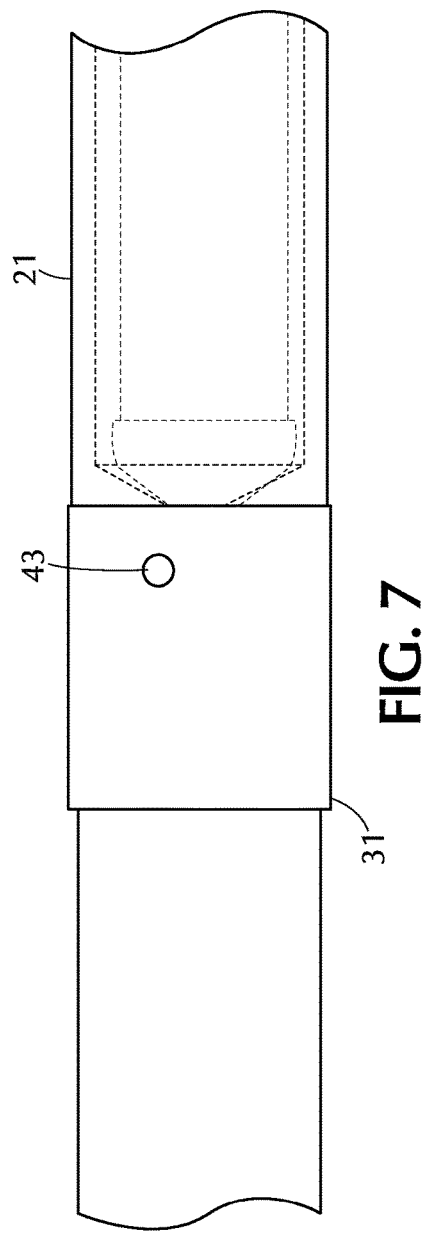
FIG. 7 is a perspective view of the second cap which attaches to the syringe assembly of FIG. 1.

Referring to FIGS. 6 and 7, the first cap 26 may be attached to the barrel 21 using at least one heat stake 43. The second cap 31 may be attached to the barrel 21 using at least one heat stake 43. The second cap 31 may be attached to the barrel 21 using at least one heat state 43.

In a specific embodiment, each of the first cap 26 and the second caps 31 is covered with a tamper-evident band 37. In one or more embodiments, the outside surface of the barrel 21 has a matte finish. The texture of the substrate on which the tamper evident band 37 will sit will influence how well the tamper evident band 37 adheres to the body of the syringe barrel 21 and to the first cap 26 and the second cap 31. A matte finish will provide a better surface for adherence of the tamper evident band 37 than a smooth/shiny surface.

Figure 8:
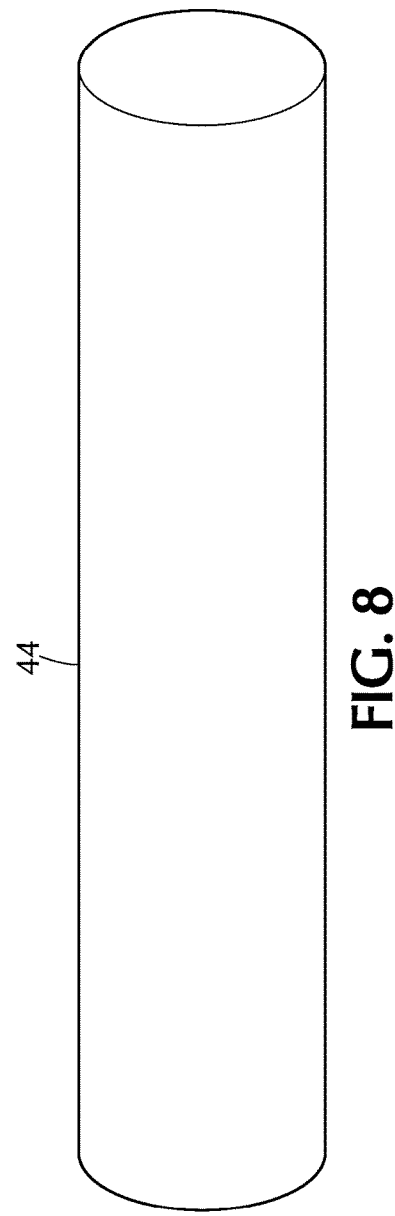
FIG. 8 is a perspective view the barrel label according to an embodiment of the present invention.

Referring to FIGS. 1 and 8, the barrel 21 may further comprise a transparent label 44 affixed to the outer surface of the side wall of the barrel 21.

The syringe assembly 20 can be sterile. The fluid path of the syringe assembly 20 can be sterilized using radiation or a gas. Radiation can include, but is not limited to, E-beam, or gamma radiation. Gamma radiation involves the use of the radioactive isotope Cobalt-60. Gas sterilization can include, but is not limited to, ethylene oxide sterilization.

In one or more embodiments, the packageless syringe assembly 20 is not surrounded by any external packaging material. External packaging material includes, but is not limited to flexible and rigid blister packs.

The syringe assembly 20 may be stored in a Tyvek® bag with a plurality of other packageless syringe assemblies.

One or more embodiments of the present invention provides for a method of sterilizing the fluid path of a syringe assembly. The method comprising subjecting a syringe assembly to radiation or a gas. The syringe assembly is as described in FIGS. 1-8. The syringe assembly can comprise a barrel including a side wall having an outside surface and an inside surface defining a chamber for retaining fluid, an open proximal end, and a distal end including a distal wall, the chamber, distal end and proximal end defining a fluid path; a plunger rod including a stopper disposed within the barrel; a first cap having a proximal end having a first segment that is radiation and gas permeable and is in flow communication with the fluid path and permitting sterilization of a portion of the fluid path by radiation or a gas, and an open distal end affixed to the proximal end of the barrel, wherein the first cap proximal end is optionally covered by a first permeable material; a second cap affixed to the distal end of the barrel, the second cap having a proximal end and a closed distal end having a second segment that is radiation and gas permeable and is in flow communication with the fluid path and permitting sterilization of a portion of the fluid path by radiation or a gas; optionally, a collar attached to the closed distal end of the second cap, the collar comprising a second permeable material that covers the closed distal end of the second cap; and a tamper-evident band covering a portion of at least one of the first and second cap.

In one or more embodiments, the sterilization of the syringe assembly is carried out using radiation. The radiation can be selected from E-beam and cobalt.

In one or more embodiments, the sterilization of the syringe assembly is carried out using gas sterilization. The gas can be ethylene oxide.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A packageless syringe assembly including a fluid path that can be sterilized by gas or radiation comprising:
   a barrel including a side wall having an outside surface and an inside surface defining a chamber for retaining fluid, an open proximal end, and a distal end including a distal wall, the chamber, distal end and open proximal end defining a fluid path;
   a plunger rod including a stopper disposed within the barrel;
   a first cap having a proximal end having a first segment that is radiation and gas permeable and is in flow communication with the fluid path and permitting sterilization of a portion of the fluid path by radiation or a gas, and an open distal end affixed to the open proximal end of the barrel, wherein the proximal end of the first cap includes a circumferential lip defining a recess containing a first permeable material;
   a second cap affixed to the distal end of the barrel, the second cap having a proximal end and a closed distal end having a second segment that is radiation and gas permeable and is in flow communication with the fluid path and permitting sterilization of a portion of the fluid path by radiation or a gas;
   a collar attached to the closed distal end of the second cap, a second permeable material extends circumferentially about a wall of the second segment and along an entire length of the second segment, wherein the second segment of the second cap extends between the collar and the proximal end of the second cap; and
   a tamper-evident band covering a portion of the open distal end of the first cap.

2. The packageless syringe assembly of claim 1, wherein the syringe assembly is not surrounded by any external packaging material.

3. The packageless syringe assembly of claim 2, wherein the external packaging material is a blister pack.

4. The packageless syringe assembly of claim 1, further comprising a plurality of openings on the first segment of the first cap that are radiation and gas permeable and are in flow communication with the fluid path and permitting sterilization of a portion of the fluid path by radiation or a gas.

5. The packageless syringe assembly of claim 4, further comprising a plurality of openings on the second segment of the second cap that are radiation and gas permeable and are in flow communication with the fluid path and permitting sterilization of a portion of the fluid path by radiation or a gas.

6. The packageless syringe assembly of claim 5, wherein the plurality of openings on the second segment of the second cap are selected from holes and slots.

7. The packageless syringe assembly of claim 5, wherein the first cap includes an interior surface having a plurality of tortuous path rings.

8. The packageless syringe assembly of claim 5, wherein the first cap is attached to the barrel using at least one heat stake.

9. The packageless syringe assembly of claim 5, wherein the second cap is attached to the barrel using at least one heat stake.

10. The packageless syringe assembly of claim 4, wherein the plurality of openings are selected from holes and slots.

11. The packageless syringe assembly of claim 10, wherein the second cap includes an interior surface having a plurality of tortuous path rings.

12. The packageless syringe assembly of claim 1, wherein the syringe assembly is sterile.

13. The packageless syringe assembly of claim 1, wherein the first permeable material comprises a medical grade material with a porosity of 8-400 seconds/100 mL.

14. The packageless syringe assembly of claim 13, wherein the first cap has a matte finish.

15. The packageless syringe assembly of claim 1, wherein the outside surface of the barrel has a matte finish.

16. The packageless syringe assembly of claim 1, wherein the second cap has a matte finish.

17. The packageless syringe assembly of claim 1, wherein the barrel further comprises a transparent label affixed to the outside surface of the side wall of the barrel.

18. The packageless syringe assembly of claim 1, wherein each of the first and second caps is covered with a tamper-evident band.

19. A packageless syringe assembly including a fluid path that can be sterilized by gas or radiation comprising:
   a barrel including a side wall having an outside surface and an inside surface defining a chamber for retaining fluid, an open proximal end, and a distal end including a distal wall, wherein the chamber, distal end and open proximal end define a fluid path;
   a plunger rod including a stopper disposed within the barrel;
   a first cap having a proximal end having a plurality of openings in flow communication with the fluid path and permitting sterilization of a portion of the fluid path by radiation or a gas and an open distal end affixed to the open proximal end of the barrel, wherein the proximal end of the first cap includes a circumferential lip defining a recess containing a first permeable material;
   a second cap affixed to the distal end of the barrel, the second cap having a proximal end and a closed distal end with a plurality of openings in flow communication with the fluid path and permitting sterilization of a portion of the fluid path by radiation or a gas;
   a collar attached to the closed distal end of the second cap, a second permeable material extends circumferentially about a wall of the second segment and along an entire length of the second segment of the second cap, wherein the second segment of the second cap extends between the collar and the proximal end of the second cap; and
   a tamper-evident band covering a portion of the open distal end of the first cap.

\* \* \* \* \*